US 8,029,183 B2

(12) United States Patent
Berelsman et al.

(10) Patent No.: US 8,029,183 B2
(45) Date of Patent: Oct. 4, 2011

(54) APPARATUS FOR MIXING BONE CEMENT

(75) Inventors: Brian K. Berelsman, Warsaw, IN (US);
John M. McDaniel, Warsaw, IN (US);
Dean E. Smeltzer, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 872 days.

(21) Appl. No.: 12/040,151

(22) Filed: Feb. 29, 2008

(65) Prior Publication Data

US 2008/0144428 A1    Jun. 19, 2008

Related U.S. Application Data

(62) Division of application No. 11/063,647, filed on Feb. 23, 2005, now abandoned.

(51) Int. Cl.
*B01F 13/06* (2006.01)
(52) U.S. Cl. ............... 366/139; 366/256; 366/260
(58) Field of Classification Search ............... 366/139, 366/189, 191, 256, 260; 222/229, 243, 246, 222/335
See application file for complete search history.

(56) References Cited

U.S. PATENT DOCUMENTS

| | | | |
|---|---|---|---|
| 29,460 A | 8/1860 | Buell | |
| 38,635 A * | 5/1863 | Weaver et al. | 366/260 |
| 85,187 A | 12/1868 | Sweeny | |
| 1,590,831 A | 6/1926 | Jones | |
| 4,721,390 A * | 1/1988 | Lidgren | 366/139 |
| 4,737,036 A | 4/1988 | Offermann | |
| 4,758,096 A | 7/1988 | Gunnarsson | |
| 5,252,301 A | 10/1993 | Nilson et al. | |
| 5,265,956 A | 11/1993 | Nelson et al. | |
| 5,328,262 A * | 7/1994 | Lidgren et al. | 366/139 |
| 5,344,232 A | 9/1994 | Nelson et al. | |
| 5,415,474 A | 5/1995 | Nelson et al. | |
| 5,431,654 A | 7/1995 | Nic | |
| 5,494,349 A | 2/1996 | Seddon | |
| 5,501,520 A | 3/1996 | Lidgren et al. | |
| 5,558,136 A | 9/1996 | Orrico | |
| 5,797,679 A | 8/1998 | Grulke et al. | |
| 5,842,786 A | 12/1998 | Solomon | |
| 5,934,803 A | 8/1999 | Hutter | |
| 6,042,262 A | 3/2000 | Hajianpour | |
| 6,176,607 B1 | 1/2001 | Hajianpour | |
| 6,254,268 B1 | 7/2001 | Long | |
| 6,312,149 B1 | 11/2001 | Sjovall et al. | |
| 6,328,262 B1 | 12/2001 | Sadeck et al. | |
| 6,406,175 B1 | 6/2002 | Marino | |
| 6,435,705 B1 | 8/2002 | Long | |
| 6,547,432 B2 | 4/2003 | Coffeen et al. | |
| 6,592,247 B1 | 7/2003 | Brown et al. | |

(Continued)

OTHER PUBLICATIONS

"Collection Under Vacuum, Only Optivac®, Only Biomet," brochure. 2004. Biomet® Orthopedics, Inc. (2 pages).

(Continued)

*Primary Examiner* — David Sorkin
(74) *Attorney, Agent, or Firm* — Harness, Dickey

(57) ABSTRACT

A method and apparatus is disclosed for forming a mixed material. For example, two components of a bone cement may be positioned in the apparatus and mixed under vacuum. An increase in pressure on one side of a movable piston can move the material for ease of access and reducing voids in the mixed material.

22 Claims, 12 Drawing Sheets

U.S. PATENT DOCUMENTS

| | | | |
|---|---|---|---|
| 6,599,293 B2 | 7/2003 | Tague et al. | |
| 6,626,912 B2 | 9/2003 | Speitling | |
| 6,648,499 B2 | 11/2003 | Jonsson | |
| 6,736,537 B2 | 5/2004 | Coffeen et al. | |
| 6,755,563 B2 | 6/2004 | Wahlig et al. | |
| 6,796,987 B2 | 9/2004 | Tague et al. | |
| 6,874,927 B2 | 4/2005 | Foster | |
| 6,945,688 B2 | 9/2005 | Huyser et al. | |
| 6,994,465 B2 | 2/2006 | Tague et al. | |
| 7,134,782 B2 | 11/2006 | Coffeen et al. | |
| 2002/0089893 A1 | 7/2002 | Huyser et al. | |
| 2002/0118596 A1* | 8/2002 | Mizutani et al. | 366/189 |
| 2003/0012079 A1 | 1/2003 | Coffeen et al. | |
| 2003/0014056 A1 | 1/2003 | Tague et al. | |
| 2003/0086332 A1 | 5/2003 | Jonsson | |
| 2003/0174576 A1 | 9/2003 | Tague et al. | |
| 2006/0087912 A1 | 4/2006 | Tague et al. | |
| 2006/0109737 A1* | 5/2006 | Wilander | 366/139 |
| 2006/0158957 A1 | 7/2006 | Coffeen | |
| 2006/0225620 A1 | 10/2006 | Murphy et al. | |
| 2006/0264967 A1 | 11/2006 | Ferreyro et al. | |
| 2008/0144428 A1 | 6/2008 | Berelsman et al. | |

OTHER PUBLICATIONS

"Fusion™ vacuum mixing bowl," brochure. 2006. Biomet® Orthopedics, Inc. (6 pages).

"The Optivac® Vaccuum Mixing System, Intelligent Simplicity" brochure. 2000. Biomet® Orthopedics, Inc. (12 pages).

* cited by examiner

APPARATUS FOR MIXING BONE CEMENT

CROSS-REFERENCE TO RELATED APPLICATIONS

This application is a divisional of U.S. patent application Ser. No. 11/063,647 filed on Feb. 23, 2005 now abandoned. The disclosure of the above application is incorporated herein by reference.

FIELD

The present teachings relate generally to a device for mixing selected components, and particularly relate to a device for mixing at least two components to form a bone cement material.

BACKGROUND

Various devices for mixing at least two components to form a compound may be provided. Many devices, however, often require various external components or multiple pieces to operate successfully, particularly if various features are provided with the device. Also, some devices may be small and require a lot of dexterity for efficient use by a selected user. Therefore, it is desirable to provide a substantially integral system to allow for mixing of various components of the material for application. Moreover, it may be desirable to mix various compounds under vacuum to reduce gas bubbles in the compound, evacuating evolved gases, and other reasons.

SUMMARY

A method and apparatus for mixing a material, that may include a plurality of components, for use and application is disclosed. The device may be used to mix a powdered polymer and a liquid monomer to allow for the formation of bone cement. The device can generally include a container that has a piston that is movable within the container. A vacuum can be formed in the container and the piston may be allowed to move after release of a seal on a selected side of the piston.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

Figure 1:
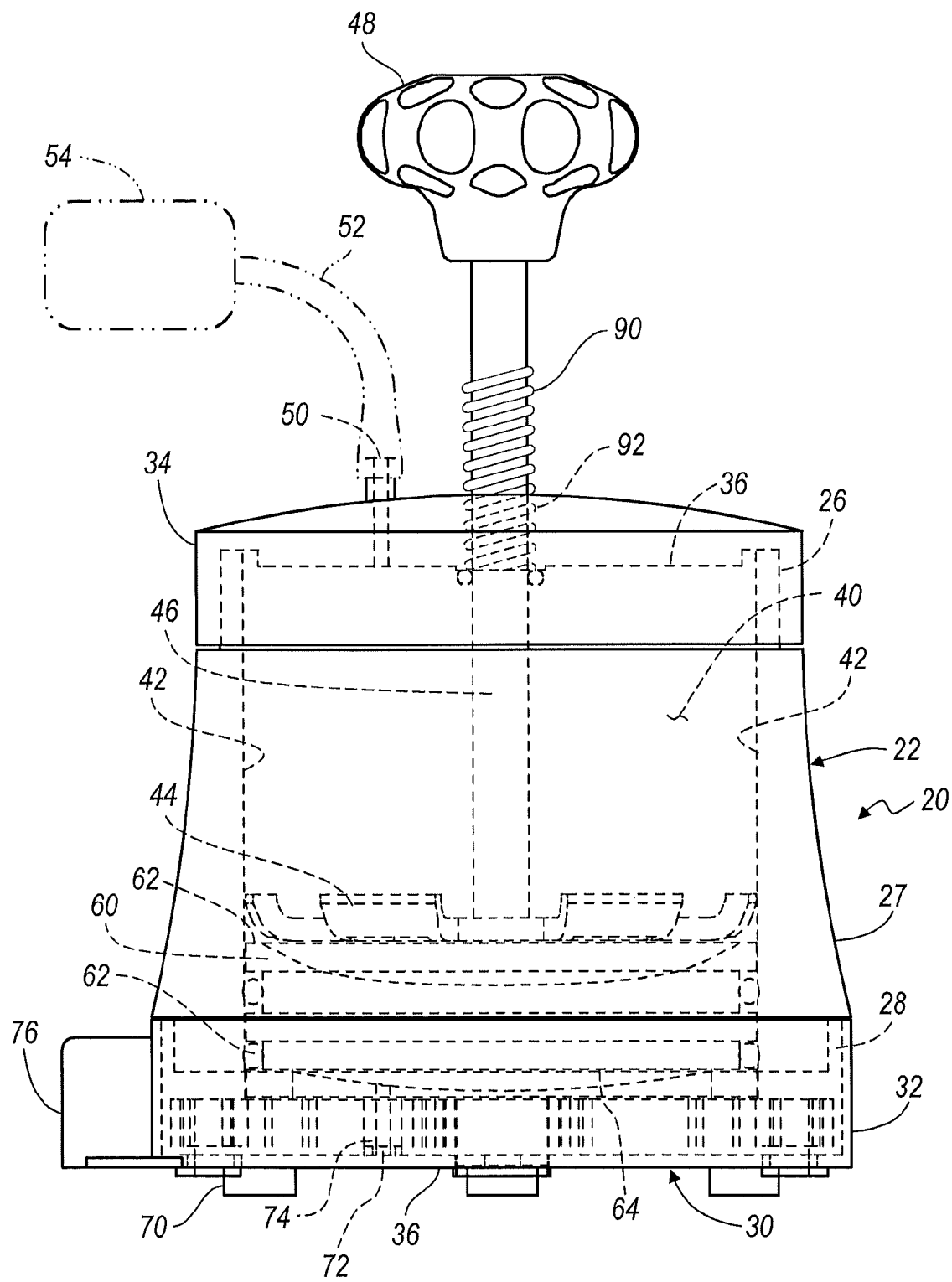
FIG. 1 is a side elevation view of a device according to various embodiments.
Figure 2:
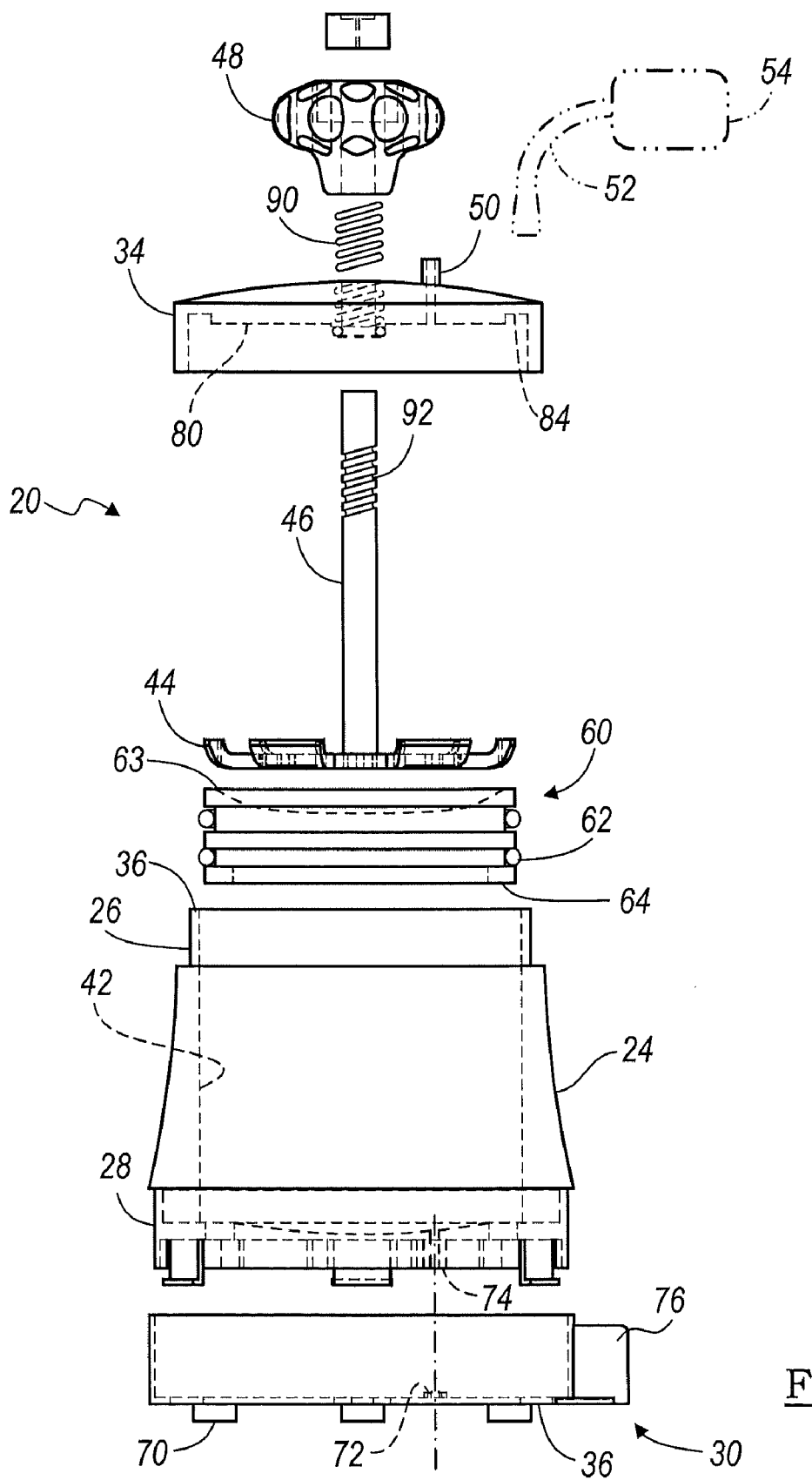
FIG. 2 is an exploded side elevational view of a device according to various embodiments.
Figure 3:
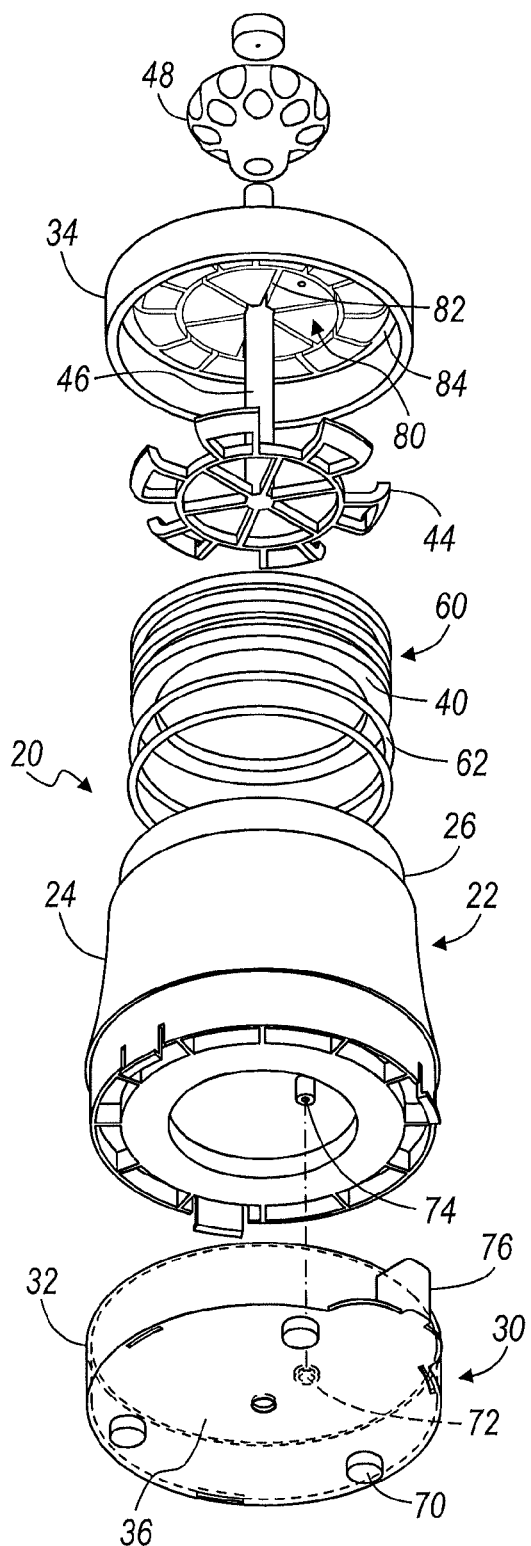
FIG. 3 is an exploded bottom perspective view of a device according to various embodiments.
Figure 4:
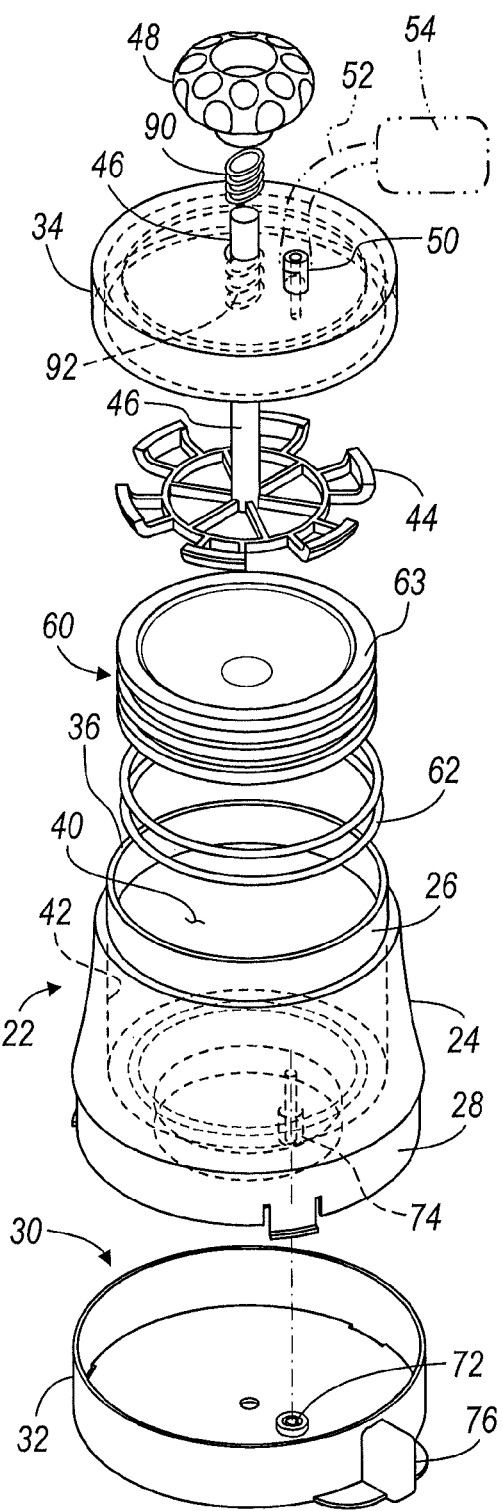
FIG. 4 is a top perspective exploded view of a device according to various embodiments.
Figure 5:
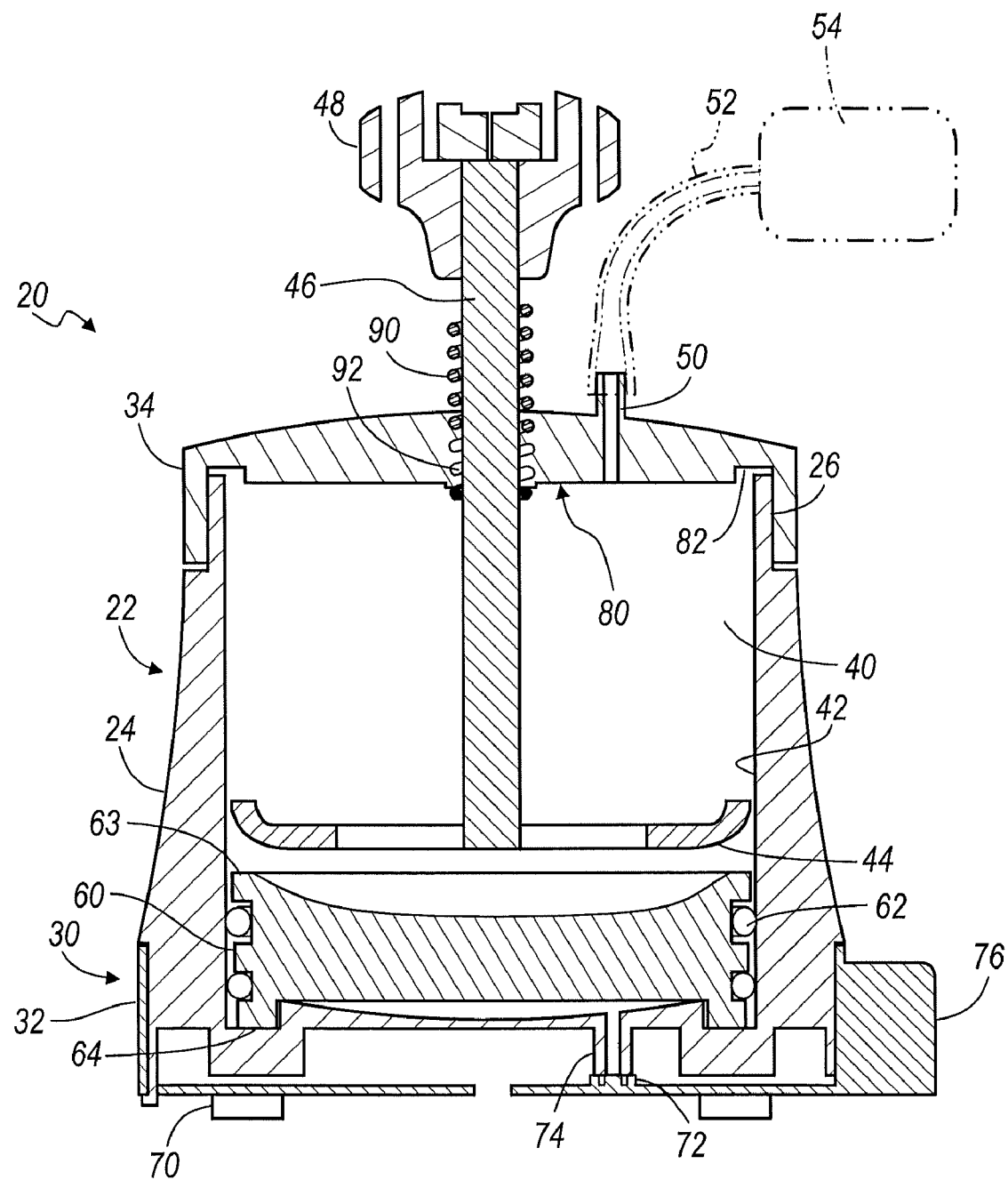
FIG. 5 is a cross-sectional assembled view of a device according to various embodiments.

The following description of the various embodiments is merely exemplary in nature and is in no way intended to limit the teachings, its application, or uses.

According to various embodiments, a device 20 may include a container, a removable sealable lid, and a removable sealable base. The lid may be sealed to the container and the base may be sealed to the container and a vacuum drawn within the container to form a reduced pressure in the container. The material may then be mixed within the container and after mixing the seal of the base may be released or removed. This allows an atmospheric pressure to form within a bottom part of the container to push up the piston that is disposed within the container. This may push and/or compress any material within the container towards a top of the container for ease of removal and to assist in removing any entrapped gases. After the piston is allowed to move a selected distance, the top of the container can be removed to equalize the pressure within the container. The material moved by the piston can then be easily accessed from the top of the container. A mixing device may also be provided in the container and may include an assisting portion, such as a spring, to assist in the mixing apparatus.

With reference to the Figures, a device 20 can be used for mixing a selected material, such as a multi-component bone cement. It will be understood that mixing a bone cement is merely exemplary and other appropriate materials may be mixed. Also the materials mixed may be two or more solids, liquids, or components of differing properties. The device 20 can include a container 22 that has an exterior wall 24. The exterior wall 24 can extend from a top of the container 26 to a bottom of the container 28. The exterior wall 24 may include an angle that tapers from the bottom 28 to the top 26. The taper may be constant or vary over the distance form the bottom 28 to the top 26. Therefore, the bottom of the container 28 can include a dimension, such as a circumference or diameter that is greater than a top of the container 26.

Although the dimension of the bottom of the container 28 may be any appropriate dimension relative to the top of the container 26, it may be selected that the bottom of the container 28 be larger than the top of the container 26. The bottom 28 can be larger than the top 26 for various reasons, such as stability, ease of grasping and holding during mixing, or other purposes.

Further, the device 20 includes a base 30 that can interconnect with the bottom 28 of the container 22. The base can include openings or passages 31 that can interact with fingers or tabs 33 that extend from the bottom 28 of the container 22. The tabs can slidingly engage the openings 31 so that the container 22 can rotate relative to the base 30, as discussed herein, to open a port 74. The fingers 33 may also, or alternatively, be disengaged from the based 30 by moving them through the openings 31. It will be understood that other appropriate mechanisms may also be provided, in addition to or alternatively to, the fingers 33 and openings 31.

The base 30 may include an exterior wall 32 that substantially continues the taper of the exterior wall 24 of the container 22 or the base 30 may include the exterior wall 32 that is substantially straight. Therefore, the base 30 may interact with the container 22 to provide a substantially continuous shape to form an aesthetically appealing apparatus. It will be understood that any appropriate shape may be provided, such as a trapezoid, a pyramid, or the like. Also the taper may be substantially conical in nature. Nevertheless, a substantially round top portion 26 and bottom portion 28 and side wall 24 that includes a taper and/or curve may be provided for both ease of use (e.g. grasping and operating) and for its aesthetic appeal to a user.

A cap 34 can also be provided to interconnect with the top portion 26 of the container 22. The cap 34 may substantially maintain the slope of the outer wall 24 of the container 22 or may be substantially perpendicular to a bottom 36 of the base 30. Therefore, the cap 34 may maintain the slope of the outer wall 24 or may provide a visually intriguing and aesthetically appealing transition from the side wall 24 to the cap 34. Further, the cap 34 may sealingly engage the container 22 by engaging an inner rim 36 that is defined by the upper portion 26 of the container 22. The inner rim 36 may include a thread, a sealing lip, a sealing member (e.g. an O-ring), or any other appropriate combination to allow for interconnection with the cap 34. For example, the cap 34 may include an internal thread and an upper rim 36 at the top 24 of the container 22 may include an external thread to offer a threadable engagement between the cap 34 and the container 22. Alternatively, or in addition thereto, a sealing member, such as an O-ring, may be provided that sealingly interconnects the cap 34 with the container 22. Nevertheless, the cap 34 may be provided to provide an airtight seal with the container 24 so that an internal portion of the container may be substantially airtight.

Defined by an interior of the container 24 is a containing area 40. The containing area may be defined by an internal wall 42 that may be any appropriate shape, or may be substantially perpendicular to the bottom portion 36 of the base 30. This may allow for various features such as a mixing paddle portion 44 that can include a substantially constant radius to mate with the interior wall 42 of the container 22. The interior wall 42 may substantially define a cylinder within the container 22. Therefore, the paddles 44 may also define a cylinder or a disk.

The paddles 44 may be interconnected with a shaft 46 that extends through the cap 34 to a handle or graspable portion 48. The paddles 44, shaft 46, and handle 48 can form a mixing system. The graspable portion 48 may be any appropriate design such as a perforated design here illustrated. Nevertheless, the aesthetic appeal of the drill-through or perforated handle design as illustrated is merely exemplary and any appropriate handle, such as a knurled handle, a t-shaped handle, or any other appropriate shape may be used. The shaft 46 can sealingly engage or interact with the cap 34 with any appropriate mechanism, such as with a sealing member 35 (e.g. an O-ring). As discussed, the handle 48 may allow a user to move the paddle 44 through the interconnection of the shaft 46 to agitate a material positioned within the containing area 40 defined by the inner wall 42. The paddles 44 can be any appropriate shape and can mate with the cap 34, as discussed herein. The sealing member can allow the interaction while maintaining a seal with the mixing area 40.

The cap 34 may also define a nipple or connection port 50 that can interconnect with a connection portion 52 to a vacuum source 54. The port can be a quick connect, threaded, Luer lock, taper lock, or any appropriate connection. It will be understood that the connection portion 52 and the vacuum source 54 is not required and any appropriate source may be used. Nevertheless, the connection port 50 can allow access to the containing area 40 from an exterior or external environment and may be used to create a vacuum within the containing area 40.

A movable or free piston 60 is provided in the containing area 40. The piston 60 can move within the mixing area 40 and may include a diameter or dimension that allows it to substantially engage the wall 42. Therefore, as the piston 60 moves within the containing area 40 it may move material that is positioned within the containing area 40 as well. The piston 60 may be further sealed to the wall 42 of the container 22 with a sealing member 62, such as an O-ring. The piston 60 can include a top 63 and a bottom 64 for various purposes. The sealing member 62 may provide for a substantially airtight seal between either side of the piston and the other side of the piston.

The piston 60 can initially rest or fit in a recess 41 defined by the mixing area 40. This can allow the paddles 44 to mix the material in the mixing area 40 while not interfering with the piston 60. Also a depression or volume 43 can be defined below the bottom 64 of the piston 60. The depression 43 can receive atmospheric gases, as described herein, to assist in moving the piston 60. The piston 60 can be moved to assist in removing various gases from the material mixed in the container 22, also as discussed herein.

The base 30 may include a foot or leg 70 that allows the base 30, or at least the bottom of the base 36, to be positioned a distance away from a surface, such as a table. Further defined by the base 30 is a sealing portion 72 that can engage or sealingly engage a second port 74 defined by the container 22. The second port 74 can engage the sealing portion 72 to further seal the container 22 from an atmosphere. Nevertheless, as discussed herein, at a selected time, the base 30 may be disengaged to move the sealing member 72 away from the second port 74 to allow for an atmosphere or other material to move into the containment area 40 or at least a portion thereof. As briefly mentioned above the base 30 can be rotated relative to the container 22 to disengage the seal or the base 30 can be removed from the container 22. In either case atmospheric gases are allowed to enter the depression 43 once the seal is broken by moving the base 30 relative to the container 22.

A signal portion 76 may be provided to indicate an orientation of the sealing member on the base 30 so that it can be properly positioned to the inlet area 74 of the container 22. As will be further discussed herein, the base 30 may be removed to allow for an inlet of atmospheric pressure through the second inlet 74 to move the piston 60 through the containment area 40. Nevertheless, the base 30 may be provided for any appropriate reason and is exemplary provided to hold and assist in holding the container 22 at a selected orientation.

The cap 34 also includes an underside 80 that can engage the paddles 44 of the mixing portion. The underside 80 may define a depression or complimentary shape 82 that is complimentary to the paddle or the paddle design 44. Therefore, the paddles can be drawn substantially into the cap 34 to provide a substantially flat surface. This may assist in maximizing the amount of material formed within the container 22, such as bone cement, and may assist in removing a maximum amount of the material from the container 22. It will be understood that the shape and structure of the paddles 44 can be any appropriate shape and structure and that the recess 82 and the lid 34 may also be any appropriate shape to compliment that of the panels 44. Further, the paddles 44 may include an angle tip or end that can engage a further recess 84 defined by the lid 80. The circumferential or annular depression 84 can be a further complimentary depression to assist in moving or holding the paddles 44 as close to the top of the lid as possible.

The handle 48 and the paddles 44 can be moved with manual power or with other assistance. For example an assisting device 90, such as a spring, can be provided to assist in moving the paddles 44. The assisting device 90 can engage any appropriate part of the device 20, such as the cap 34 and the handle 48. This may be helpful because the material formed in the container 22 is rather stiff and viscous. Also, a path 92 may be defined in the shaft 46 that can engage a projection from the cap 34, or vice versa (i.e. the groove 92 may be in the cap 34 and a projection from the shaft 46). In other words, the shaft 46 can be made or urged to move in a selected manner, such as twisting, as it is moved in and out of the container 22.

It will be understood that the container 22 can be designed in any appropriate manner and the gentle sloping shape of the outside wall 24 and the complimentary or contrasting fits of the base 30 and the cap 34 provide an aesthetically pleasing composition that is not necessary for functionality. Although the device 20 has been described above, a selected method will be described below. It will be understood that the method of using the device 20, as described herein, is merely exemplary and is not limiting as to possible methods or uses of the device 20.

With reference to FIGS. 8-11 the device 20 including the cap 34 and the opening defined by the upper rim 36 may be useful for various applications where access to a large volume of the mixed material, which can be bone cement, at a particular time is desirable. Although the container 22 or the device 20 can be used to create any appropriate material, it may be selected to form bone cement in the device 20. The large opening at the upper end of the container 22 can allow for easy access, such as with a spatula 100 or other spreading device, to obtain a selected volume of the material and position it and spread it as desired The device 20 may be provided in a selectively sterile container or apparatus 120, as illustrated in FIG. 12. Nevertheless, the container 120 need not be sterilized prior to use or supply to a user. The container 120 may also include all of the components to make a selected compound, such as a bone cement. Therefore the container or kit 120, may include the device 20, a powder component 122, a liquid component 124 (e.g. a monomer), the spreading spatula 100, and may also include the vacuum source 54 and the vacuum connection 52. It will be understood that the kit 120 may include any appropriate portions.

Although the device 20 need not be provided in a sterile container, it may be sterilized on site, it may be selectively be provided in a sterile manner. The device 20 can be formed of any appropriate materials including metals (e.g. stainless steel), polymers, or any appropriate material. Generally, the device 20 is able to contain the volume of the selected material, such as the bone cement, and can withstand a selected heat produced in the device 20. Further, the device 20 can be formed of a material that can be sterilized in general hospital sterilization techniques, such as autoclave, or sterilized in other manners such as radiation sterilization.

Figure 6:
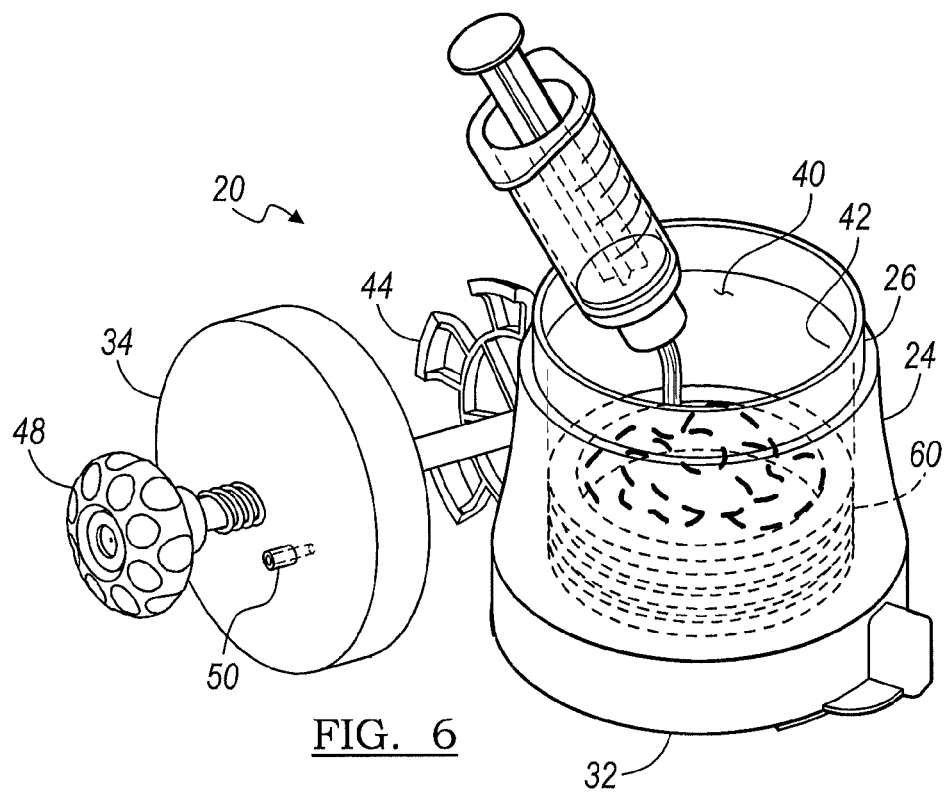
FIG. 6 is an open environmental view of a device according to various embodiments.

The device 20 generally allows for a selected material or combinations of materials to be positioned in the mixing area 40 of the container 22. The base 30 may be interconnected with the bottom portion 28 of the container 22 such that the sealing portion 72 seals the second port 74 for a selected amount of time. With reference to FIG. 6, the components may then be positioned through the top of the container 22 into the mixing area 40 prior to mixing. The indicator 76 may include a marking to show the sealed and unsealed position of the base 30 relative to the container 22, thus a user can determine the appropriate position of the container 22 relative to the base 30.

Figure 7:
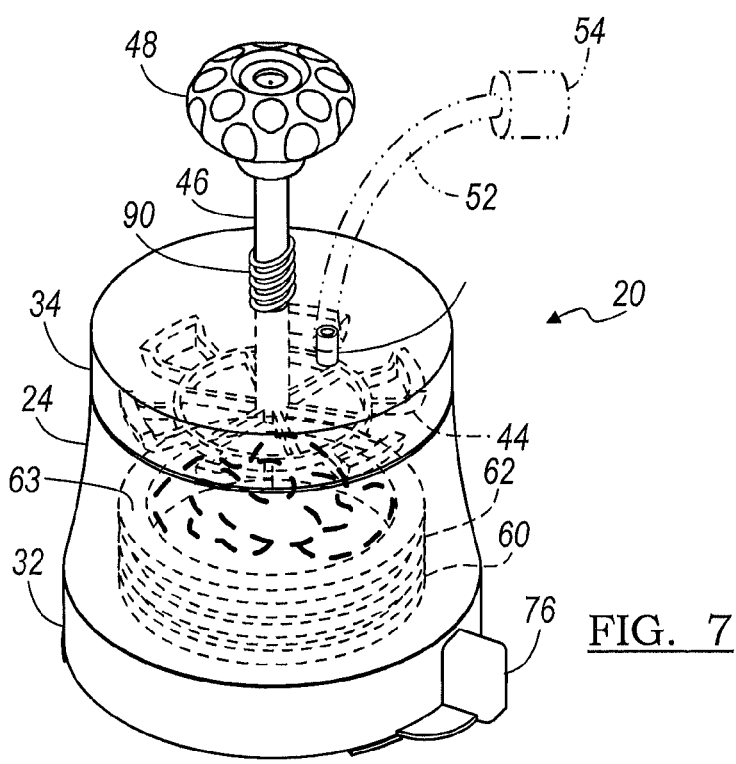
FIG. 7 is a top perspective view of a device according to various embodiments.
Figure 8:
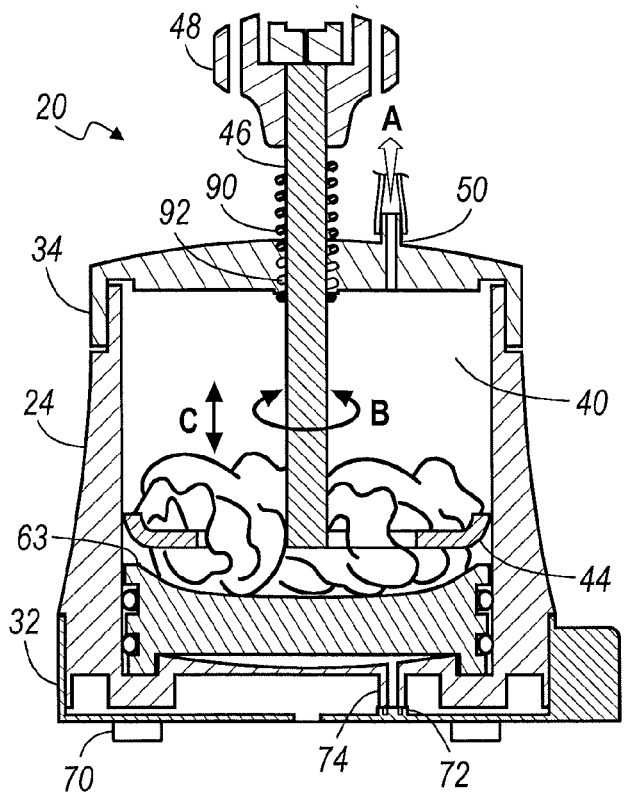
FIG. 8 is a cross-sectional environmental view of a device according to various embodiments in use.

As discussed above, the cap 34 can be sealingly engaged to the container 22. For example, the cap 34 may be threaded on to the container to provide a substantially airtight seal through the interior of the container 40. Therefore, the various components of the material to be mixed can be positioned in the mixing area 40 and the cap 34 can be sealingly engaged with the container 22. After this occurs, with reference to FIG. 7, the vacuum source 54 can be interconnected with the container 22 with the connection 52 connected to the port 50. The vacuum source 54 can be used to draw a vacuum in the mixing area 40 to withdraw most of the gases, generally in the direction of Arrow A, within the holding area 40 and to reduce a pressure in the mixing area 40. Further, the vacuum source 54 can be maintained to withdraw any gases that may evolve during the mixing of the various components within the mixing area 40. Once a sufficient vacuum is formed, with reference to FIG. 8, the paddles 44 can be actuated with the handle 48 and the shaft 46 to assist in mixing the components. The handle 48 can move the shaft 46 and the paddles 44 in the direction of arrows B and/or C. Also the spring 90 and the groove 92 may assist in this motion.

As discussed above, the spring 90 can be provided to assist in moving the handle back to a relaxed or first position, such as that moving it from the pressed in position. Further, the track 92 defined in the shaft 46 can interact with a portion defined by the cap 34 to assist in the shaft 46 rotating, which then rotates the paddles 44. Therefore, each time the handle 48 and the shaft 46 are depressed, the shaft rotates thus rotating the paddles 44 and the spring 90 assists in drawing the paddles 44 and the shaft 46 back up to a relaxed position. Therefore, the mixing of the material within the mixing area 40 can be a substantially single action of pushing the handle 48 down and allowing the spring 90 to retract the handle from the pressed position. The track 92 assists in rotating the shaft 46 and the paddles 44 and thus assists in mixing the components in the container 40. It will be understood, however, that the user may also assist in rotating the handle 48 which would rotate the shaft 46 and the paddles 44. The spring 90 and the track 92 is for ease of operation and can be eliminated or augmented with other apparatuses. For example, a motor may be interconnected with the shaft 46 such that the mixing of the material in the mixing area 40 is performed with a motor or powered device.

Figure 9:
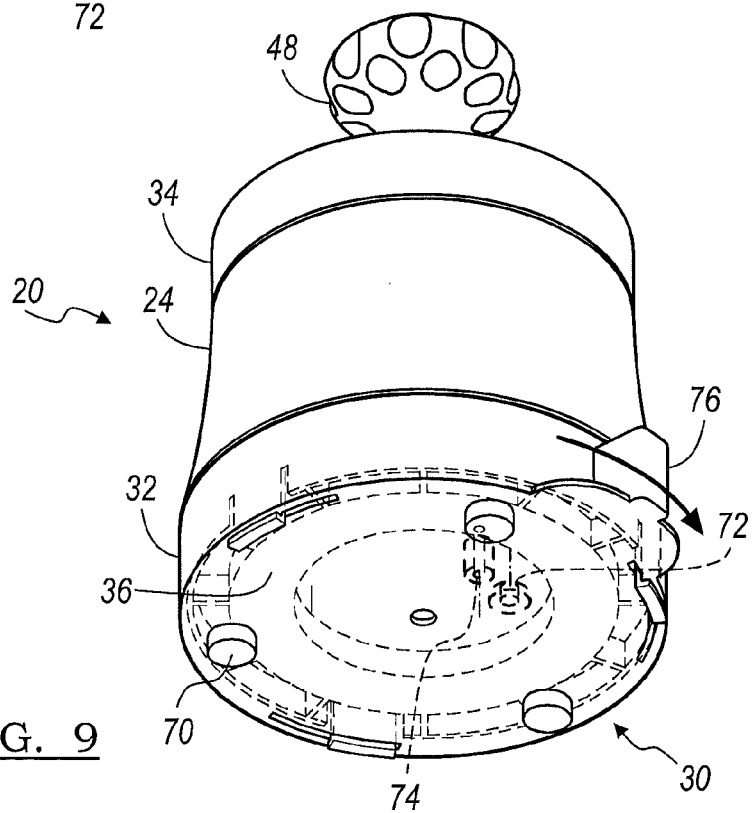
FIG. 9 is a bottom perspective view of a device according to various embodiments.

Regardless, the paddles 44 may assist in mixing the components positioned in the mixing area 40. After a selected mixing time, or when a selected property of the material is achieved, the mixing with the paddles 44 can be stopped. Once the mixing is completed, the paddles 44 can either be drawn into the recesses defined by the cap 34, if the recesses 82, 84 are provided, or the paddles 44 may be left within the mixing area 40. With reference to FIG. 9, the base 30 can then be rotated, or otherwise moved, to disengage the seal to allow atmospheric gases through the port 74, generally in the direction of Arrows D, and into the depression 43. This can cause the piston 60 to be moved nearer the top 26 of the container 22 with a pressure differential.

Figure 10:
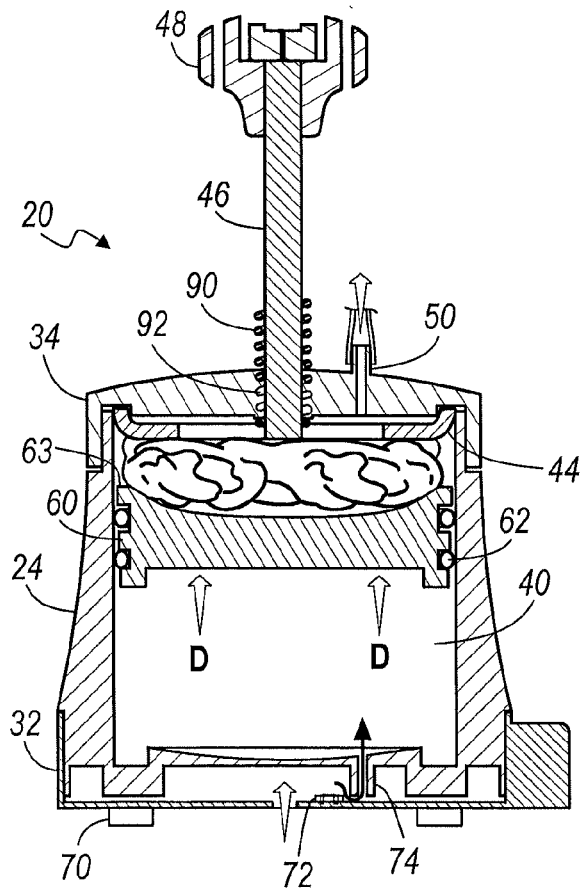
FIG. 10 is a cross-sectional environmental view of a device according to various embodiments.

With reference to FIG. 10, maintaining the vacuum in the mixing area 40 and disengaging the seal 72 from the inlet 74 can cause the pressure differential. The vacuum can be maintained by having a one way valve with the port 50 or maintaining the vacuum source 54 while releasing the seal by moving the base 30 relative to the container 22. The base 30 can be disengaged from the bottom 28 of the container 22 in any appropriate manner. For example, locking tabs can be used to interconnect the base 30 with the container 22 and then be disengaged to move the base 30 away from the container 22 or to rotate the base 30 relative to the container 22. This allows for gasses to move into the port 74 and the depression 43 under atmospheric pressure and push against a bottom side 64 of the piston 60.

As atmospheric pressure moves into the inlet 74, the pressure differential causes the piston 60 to move towards the top 26 of the container 22. As discussed above, the piston 60 may be substantially sealed or engaged at the inner wall 42 of the container 22 to assist in moving material positioned in the mixing area 40 towards the top 26 of the container 22. This assists in forcing gases out of the material and the mixing area 40 that may have formed during the mixing. Also any bubbles in the compound can be evacuated to a selected degree. If the paddles 44 are not drawn near the cap 34, the movement of the piston 60 may also move the paddles 44, the shaft 46, and the handle 48 upwards as well.

After a selected time, or when the pressure of the material in the mixing area 40 is great enough to equal the pressure of the atmospheric pressure pushing on the piston 60, the piston 60 will substantially stop moving. Either at this point or after a selected period of time, the vacuum connector 52 may be disengaged from the inlet 50 to equalize the pressure above the piston 60 to the pressure below the piston 60. After this, the cap 34 can be removed. It will be understood that in removing the cap 34, the pressure may also equalize thus allowing removal of the cap 34 from the device 20.

Figure 11:
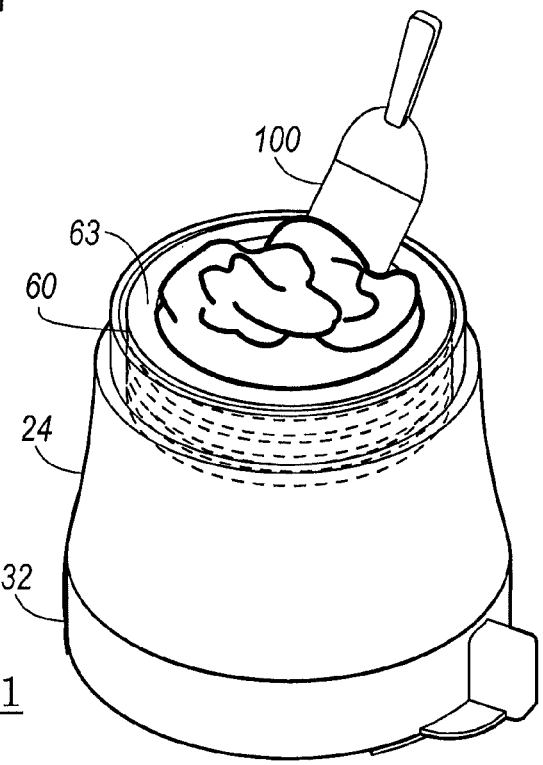
FIG. 11 is an perspective view of a device according to various embodiments in use.
Figure 12:
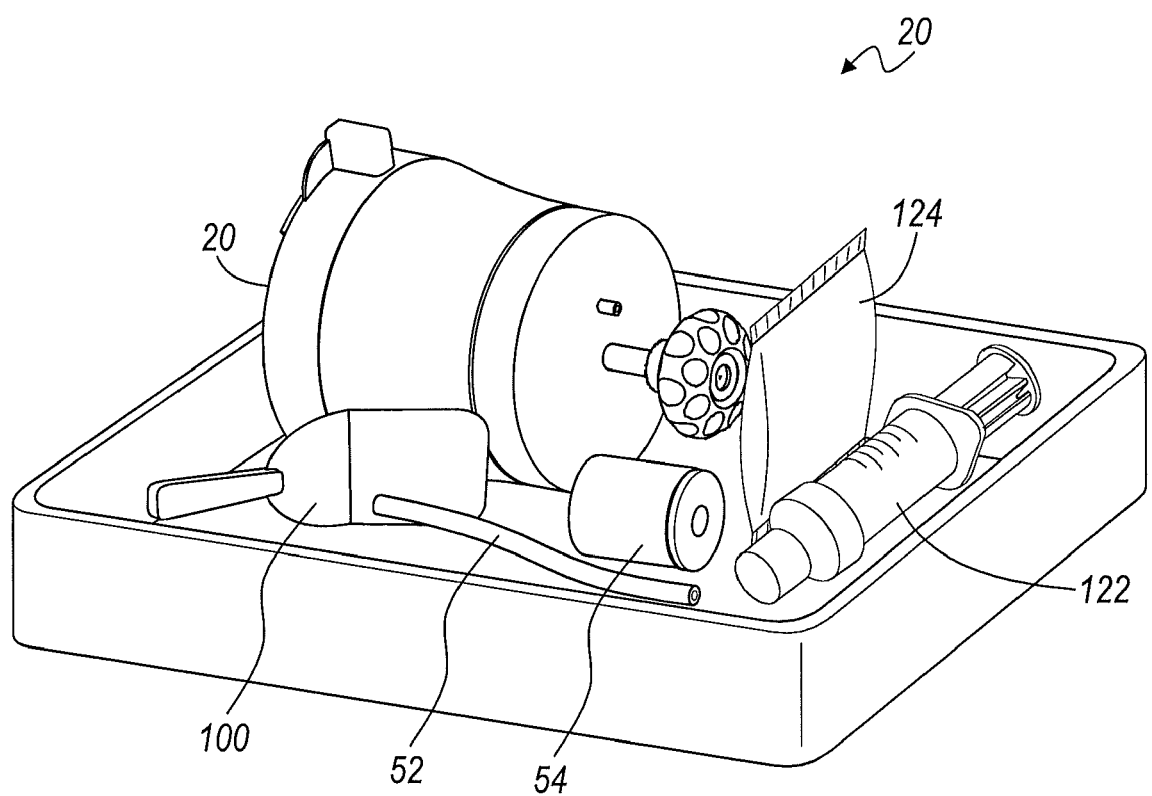
FIG. 12 is a kit including a device and various components according to various embodiments.
Figure 13:
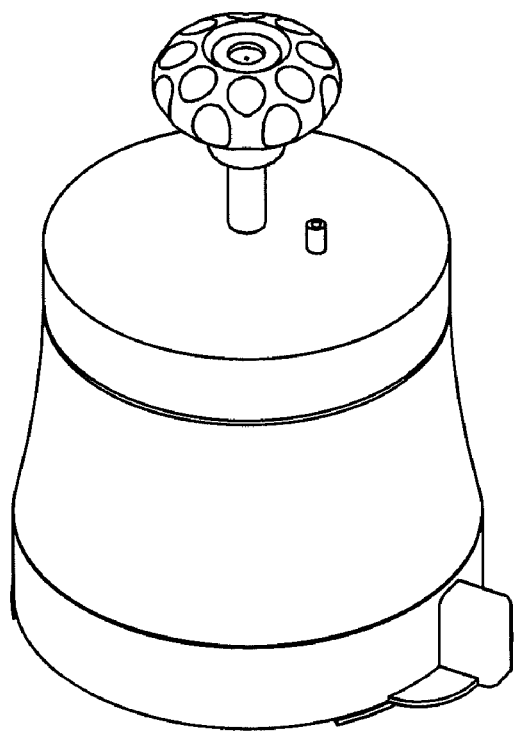
FIG. 13 is a top perspective view of a device according to various embodiments.
Figure 14:
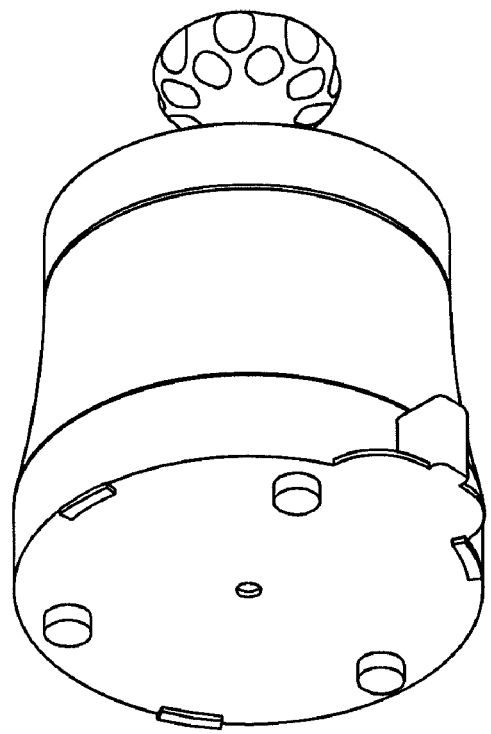
FIG. 14 is a bottom perspective view of a device according to various embodiments.
Figure 15:
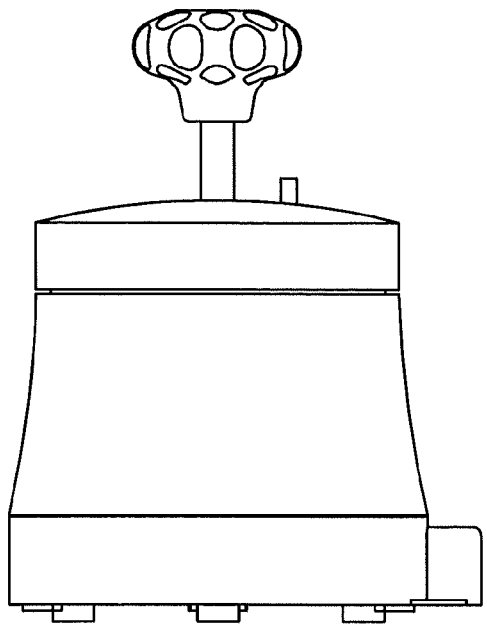
FIG. 15 is a side elevational view of a device according to various embodiments.
Figure 16:
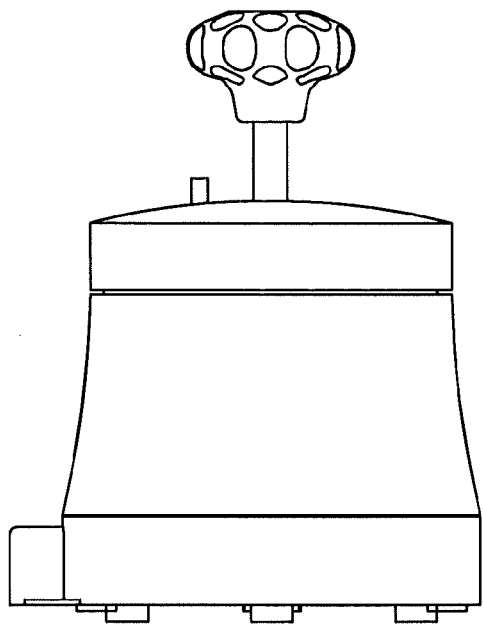
FIG. 16 is a side elevational view of a device according to various embodiments.
Figure 17:
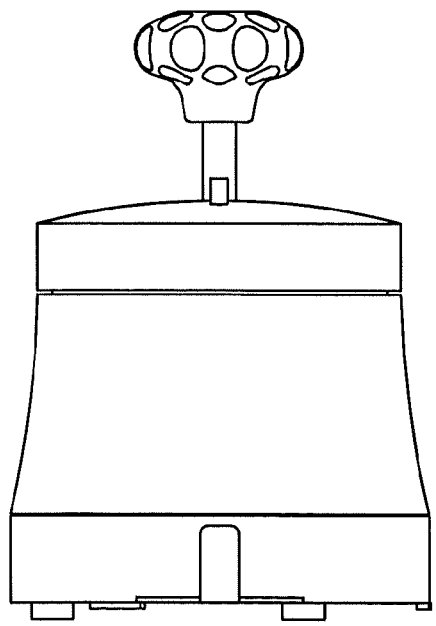
FIG. 17 is a side elevational view of a device according to various embodiments.
Figure 18:
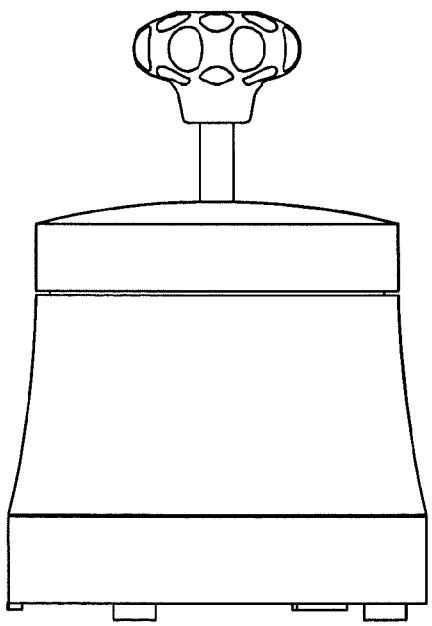
FIG. 18 is a side elevational view of a device according to various embodiments.
Figure 19:
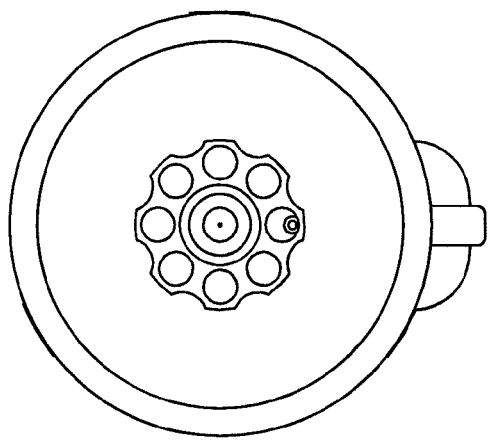
FIG. 19 is a top elevational view of a device according to various embodiments.
Figure 20:
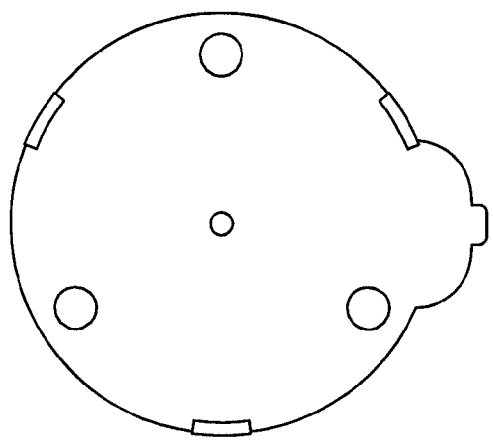
FIG. 20 is a bottom elevational view of a device according to various embodiments.
Figure 21:
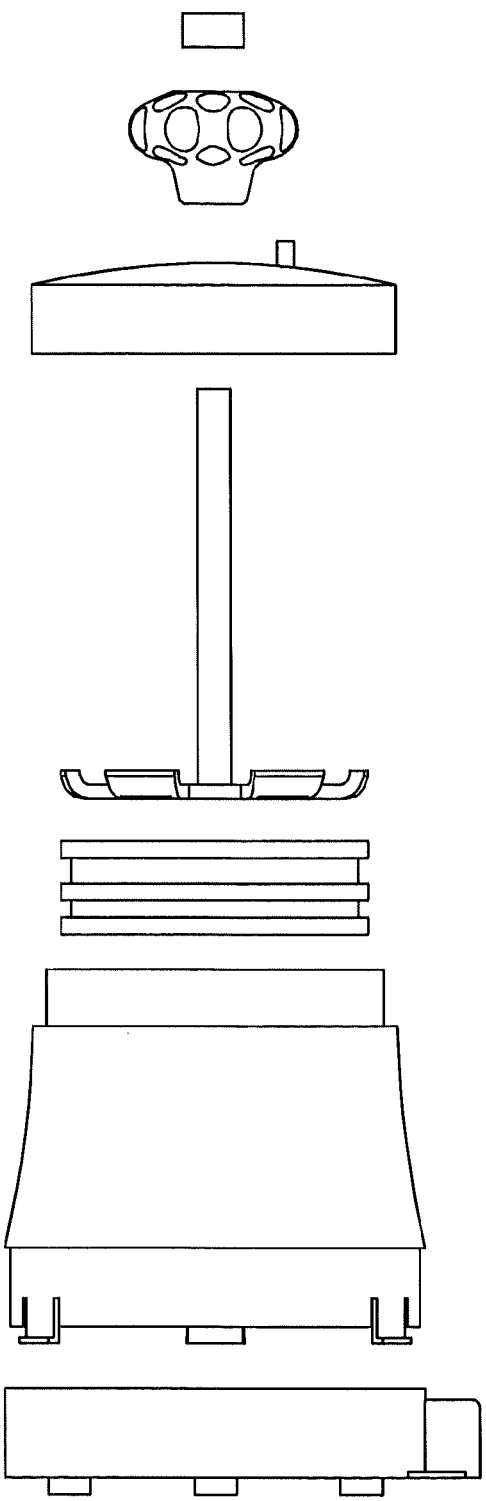
FIG. 21 is an exploded side elevational view of a device according to various embodiments.
Figure 22:
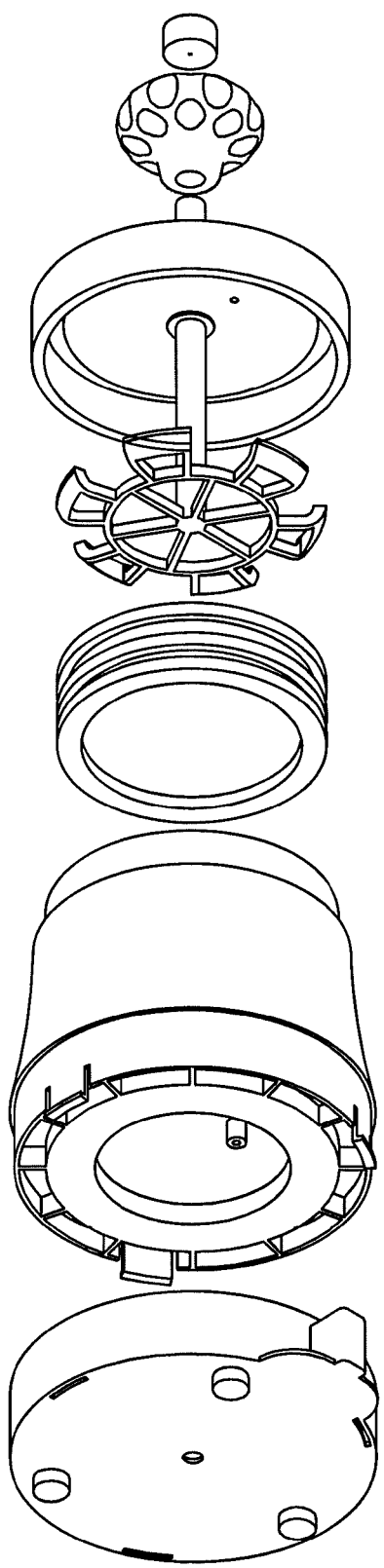
FIG. 22 is an exploded bottom perspective view of a device according to various embodiments.
Figure 23:
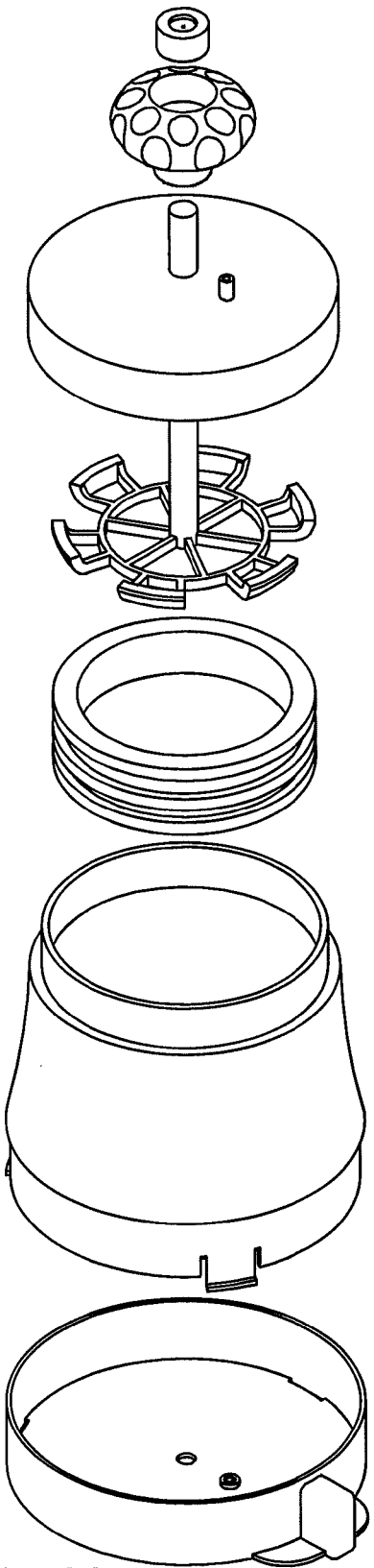
FIG. 23 is an exploded top perspective view of a device according to various embodiments.

With reference to FIG. 11, once the cap 34 is removed, access can be had to the mixed material that is within the container 22, for example with the spatula 100. The piston 60 can act as a base by holding the mixed material at the level which is reached within the container 22 and the sealing member 62 may also assist in holding the piston 60 at the selected location. Therefore, the mixed material can be easily accessed through the top of the container 22 for various applications.

As illustrated in FIG. 11 the material may be easily accessed and scooped out with a selected spatula or other device for application in various procedures. For example, the device 20 can be used to mix bone cement components for use in an implantation procedure, such as in positioning a femoral component on a femur. According to various embodiments, the mixed cement may be applied or smeared on the femoral component before the femoral component is positioned on the distal end of the femur. Thus, a large access area can be used for ease of use during application of the mixed bone cement.

It will be understood that the device 20 can be used to mix any appropriate material such as bone cement, biological components, or the like. Regardless, the material can be mixed under vacuum for various reasons, such as reducing fumes, decreasing gases in the formed material, and reducing porosity in the final component. Further, the movable piston 60 can assist in reducing porosity in a mixed component by assisting in decreasing any bubbles or voids that are at reduced pressure due to the vacuum because the piston 60 substantially presses the material against the cap 34 thereby reducing the void areas.

The description is merely exemplary in nature and, thus, variations that do not depart from the gist of the teachings are intended to be within the scope of the teachings. Such variations are not to be regarded as a departure from the spirit and scope of the teachings.

What is claimed is:

1. A device to assist in mixing a material under a reduced pressure, comprising:
   a container including an inner wall defining a mixing area and a passage through the inner wall;
   a mixing system;
   a cap operable to be sealed substantially air tight to the container through which at least a portion of the mixing system extends;
   a piston moveable by a pressure differential formed in the container; and
   a base moveable relative to the container and a sealing portion defined by the base;
   wherein the base is moveable from a sealed position to an unsealed position relative to the passage;
   wherein the pressure differential is operable to be developed in the container to urge the piston towards the cap when the base is moved to the unsealed position.

2. The device of claim 1, further comprising:
   a rebounding mechanism to assist in moving the mixing system; and
   wherein the rebounding mechanism assists in moving the mixing system in at least one direction relative to the container.

3. The device of claim 2, further comprising:
   a top wall;
   wherein the rebounding mechanism includes a spring;
   wherein the mixing system includes a rod and a mixing paddle portion;
   wherein the spring is disposed around the rod connected to the mixing system and engages the top wall to rebound the rod to a selected position when moved by an external force.

4. The device of claim 1, wherein the container includes:
   an exterior wall that extends from a top of the container to a bottom of the container;
   wherein the exterior wall includes an angle that tapers towards a central axis of the container from the bottom to the top so that the bottom of the container includes a dimension that is greater than a top of the container.

5. A device to assist in mixing a material under a reduced pressure, comprising:
   a container including an inner wall defining a mixing area;
   a mixing system including a mixing paddle portion;
   a cap operable to be sealed substantially air tight to the container through which the mixing system extends and wherein an internal surface of the cap substantially facing the inner wall of the container defines a depression substantially complementary to a shape of the mixing paddle portion so that the mixing paddle portion can be drawn substantially into the depression defined by the internal surface of the cap to provide a substantially flat surface when the mixing paddle portion is drawn into the depression in the internal surface of the cap to assist in maximizing material removal from the container;

a piston moveable by a pressure differential formed in the container by operating a portion of the container; and a base moveable relative to the container;

wherein a pressure differential is operable to be developed in the container to urge the piston towards the cap when the base is moved to an unsealed position.

6. The device of claim 1, wherein the mixing system includes a shaft;

wherein one of the shaft or the cap defines a projection and the other of the shaft or the cap defines a path;

wherein the projection and the path are operable to cooperate to urge the shaft in a selected manner via the interaction of the path and projection.

7. The device of claim 1, wherein the inner wall includes a bottom wall that defines the passage;

wherein the base is moveably interconnected near the bottom wall of the container;

wherein the passage is operable to be sealed by the sealing portion upon rotating the base relative to the container.

8. A device to assist in mixing a material under a reduced pressure, comprising:

a container having an inner wall defining a mixing area and an exterior wall extending from a first end of the container to a second end of the container;

a mixing system;

a cap operable to be sealed substantially air tight near the first end of the container through which the mixing system extends;

a piston moveable by a pressure differential formed in the container;

a port having a port wall defining a throughbore extending from the inner wall; and a base moveably interconnected with the container near the second end of the container; and a sealing member extending from the base;

wherein the sealing member is operable to move from a first sealed position in cooperation with said port to a second unsealed position.

9. The device of claim 8, wherein the base includes passages that interact with a tab that extends from the container;

wherein the tabs slidingly engage the passages so that the container can rotate relative to the base.

10. The device of claim 8, wherein the base is operable rotate between a sealed position where the sealing member seals the port and an unsealed position where the sealing member does not seal said port.

11. The device of claim 8, wherein when a pressure is lower between a first side of the piston and the first end of the container than between a second side of the piston and the second end of the container;

wherein the port is unsealed and the piston is operable to move towards the lower pressure area creating a void between the second side of the piston and the second end of the container;

wherein the base is operable to be rotated to maintain the void even when the pressure differential does not exist.

12. The device of claim 8, further comprising:

a vacuum source operable to create an area of relatively low pressure within the container.

13. The device of claim 8, further comprising:

a signal portion to indicate whether the sealing member is in the sealed position or the unsealed position relative to the port.

14. A device to assist in mixing a material under a reduced pressure, comprising:

a container having an inner wall defining a mixing area and an exterior wall extending from a first end of the container to a second end of the container;

a cap operable to substantially seal the container;

a mixing system operable to extend through the cap;

a piston moveable by a pressure differential formed in the container, wherein the piston is operable to separate the container into a first area operable to contain a mixed material and a second area devoid of the mixed material; and a base moveably interconnected near the second end of the container;

a port defined in the inner wall defining a passage between the second area and the base; and a sealing member defined by the base operable to seal the port when the base is in a sealed position;

wherein when the base is in the sealed position the piston is substantially fixed relative to the inner wall to define the first area and the second area.

15. The device of claim 14, further comprising:

a vacuum system operable to form the pressure differential within the container;

wherein a first pressure in the first area is operable to be lower than a second pressure in the second area.

16. The device of claim 14, wherein the mixing system includes a shaft that defines a path to engage a projection member extending from the cap to direct at least one movement of the shaft relative to the cap.

17. The device of claim 14, further comprising:

a signal portion to provide a visual indication of whether the base is in the sealed position or an unsealed position.

18. The device of claim 14, further comprising:

wherein the port has a port wall defining a throughbore extending from the inner wall towards the second end of the container; and wherein sealing member extends from the base and is operable to engage the port wall to seal the port.

19. The device of claim 14, wherein the mixing system includes a mixing paddle portion;

wherein a surface of the cap defines a depression substantially complimentary to the mixing paddle portion so that the mixing paddle portion can be drawn substantially into the depressions defined by the surface of the cap.

20. The device of claim 19, wherein the paddle portion includes at least one annular ring and a spoke extending from the shaft;

wherein the depression includes at least one annular depression and one spoke depression.

21. The device of claim 14, wherein the mixing system includes a mixing paddle portion;

wherein the piston includes a surface that is substantially complimentary to a shape of a surface of the mixing paddle portion.

22. The device of claim 14, further comprising:

a depression defined by the container at the second end to moveably receive a portion of the base wherein an exterior surface of the exterior wall and a base exterior surface are substantially continuous;

wherein the second end of the container is broader than the first end.

* * * * *